United States Patent
Klima et al.

(10) Patent No.: US 10,201,422 B2
(45) Date of Patent: *Feb. 12, 2019

(54) DELIVERY SYSTEM FOR COLLAPSIBLE HEART VALVE

(71) Applicant: St. Jude Medical, LLC, Abbott Park, IL (US)

(72) Inventors: Daniel J. Klima, Andover, MN (US); Huisun Wang, Maple Grove, MN (US); Ralph J. Thomas, Champlin, MN (US); Gary W. Geiger, Fridley, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 268 days.

This patent is subject to a terminal disclaimer.

(21) Appl. No.: 15/218,220

(22) Filed: Jul. 25, 2016

(65) Prior Publication Data

US 2016/0331533 A1 Nov. 17, 2016

Related U.S. Application Data

(63) Continuation of application No. 13/211,486, filed on Aug. 17, 2011, now Pat. No. 9,700,411.

(Continued)

(51) Int. Cl.
*A61F 2/24* (2006.01)
*B29C 70/68* (2006.01)
(Continued)

(52) U.S. Cl.
CPC ...... *A61F 2/2436* (2013.01); *A61B 17/00234* (2013.01); *A61B 2017/00314* (2013.01); *A61F 2/966* (2013.01); *Y10T 156/1043* (2015.01)

(58) Field of Classification Search
CPC ........ A61F 2/2427; A61F 2/2436; A61F 2/95; A61F 2/962; A61F 2/966
See application file for complete search history.

(56) References Cited

U.S. PATENT DOCUMENTS 6,019,778 A 2/2000 Wilson et al.
6,645,238 B2 11/2003 Smith
(Continued)

FOREIGN PATENT DOCUMENTS

WO 9638193 A1 12/1996
WO 2007005799 A1 1/2007
(Continued)

OTHER PUBLICATIONS

Australian Examination Report for Application No. 2011292460 dated Aug. 9, 2013.
(Continued)

*Primary Examiner* — Todd Scherbel
(74) *Attorney, Agent, or Firm* — Lerner, David, Littenberg, Krumholz & Mentlik, LLP

(57) ABSTRACT

A delivery system for delivering a collapsible prosthetic heart valve includes a valve support structure for supporting a collapsible prosthetic heart valve, and a distal sheath movable in a longitudinal direction relative to the valve support structure between a first position in which the distal sheath is adapted to surround a collapsible prosthetic heart valve supported on the valve support structure, and a second position in which the distal sheath is adapted to expose the collapsible prosthetic heart valve for deployment. The distal sheath is at least partially formed of an inner polymer layer, an outer polymer layer, and a tubular supporting member sandwiched between the inner polymer layer and the outer polymer layer.

14 Claims, 7 Drawing Sheets

Related U.S. Application Data

(60) Provisional application No. 61/374,458, filed on Aug. 17, 2010.

(51) Int. Cl.
    *A61B 17/00* (2006.01)
    *A61F 2/966* (2013.01)

(56) References Cited

U.S. PATENT DOCUMENTS

| | | |
|---|---|---|
| 6,890,317 B2 | 5/2005 | Gerdts et al. |
| 6,942,688 B2 | 9/2005 | Bartholf et al. |
| 9,700,411 B2 * | 7/2017 | Klima .................. A61F 2/2436 |
| 2005/0273151 A1 | 12/2005 | Fulkerson et al. |
| 2007/0088424 A1 | 4/2007 | Greenberg et al. |
| 2008/0147179 A1 | 6/2008 | Cai et al. |
| 2008/0188928 A1 | 8/2008 | Salahieh et al. |
| 2010/0145309 A1 | 6/2010 | Tollner et al. |
| 2010/0168834 A1 | 7/2010 | Ryan et al. |
| 2011/0098804 A1 | 4/2011 | Yeung et al. |

FOREIGN PATENT DOCUMENTS

| | | |
|---|---|---|
| WO | 2009091509 A1 | 7/2009 |
| WO | 2011035327 A1 | 3/2011 |

OTHER PUBLICATIONS

International Search Report for Application No. PCT/US2011/001443 dated Apr. 19, 2012.

* cited by examiner

DELIVERY SYSTEM FOR COLLAPSIBLE HEART VALVE

CROSS-REFERENCE TO RELATED APPLICATIONS

The present application is a continuation of U.S. patent application Ser. No. 13/211,486, filed on Aug. 17, 2011, which claims the benefit of the filing date of U.S. Provisional Application No. 61/374,458, filed Aug. 17, 2010, the disclosures of which are hereby incorporated by reference herein.

BACKGROUND OF THE INVENTION

The present disclosure relates to heart valve replacement and, more specifically, to devices, systems and methods for implanting a collapsible prosthetic heart valve in a patient.

A healthy aortic valve acts as a one-way valve, opening to allow blood to flow out of the left ventricle of the heart, and then closing to prevent blood from flowing back into the heart. Diseased or damaged aortic valves may not close properly and thus allow blood to flow into the heart. Damage to aortic valves may occur due to congenital defects, the natural aging process, infection or scarring. Diseased or damaged aortic valves sometimes need to be replaced to prevent heart failure. In such cases, collapsible prosthetic heart valves may be used to replace the native aortic valve.

Current collapsible prosthetic heart valve designs may be used in high-risk patients who may need a cardiac valve replacement, but who are not appropriate candidates for conventional open-chest, open-heart surgery. These collapsible and re-expandable prosthetic heart valves can be implanted transapically or percutaneously through the arterial system. One percutaneous delivery method entails introducing a collapsible prosthetic heart valve through a patient's femoral artery. This delivery method is referred to as a transfemoral approach.

A collapsible prosthetic heart valve may be delivered into a patient via a tube-like delivery apparatus such as a catheter, a trocar, a laparoscopic instrument, or the like. To place such a valve into a delivery apparatus and ultimately into a patient, the valve must first be collapsed or crimped to reduce its circumferential size. The delivery apparatus is then introduced transapically or percutaneously into a patient until it reaches the implantation site.

When a collapsed heart valve has reached the desired implantation site in the patient (e.g., at or near the annulus of the patient's heart valve that is to be replaced by the prosthetic valve), the prosthetic heart valve can be released from the delivery apparatus and re-expanded to its full operating size.

While various improvements have been made to collapsible prosthetic heart valve delivery devices, conventional delivery devices, systems, and methods still suffer from some shortcomings. For instance, conventional delivery systems may not properly align the prosthetic heart valve with the valve annulus. A misaligned prosthetic heart valve may cause paravalvular (PV) leaks.

As stated above, collapsible prosthetic heart valves may be delivered to the valve annulus, and particularly the aortic valve annulus, either transfemorally or transapically. With either technique, however, it is difficult to properly align the collapsible heart valve with the valve annulus.

In transfemoral valve implantation, the collapsible prosthetic heart valve is delivered in a retrograde manner from the femoral artery through the aortic arch to the native aortic valve annulus. The distal sheath of the delivery catheter is bent significantly to pass through the aortic arch, which significantly biases the sheath toward the outside wall of the aortic arch. This may cause the prosthetic heart valve to be deployed out of alignment with the aortic annulus. One way to solve this problem is to employ a steerable catheter. Steerable catheters, however, can be expensive to make and more complicated to use. Another problem with steerable catheters is that the section that has to be deflected is on the distal sheath of the delivery system. It is very difficult to deflect the distal sheath because the collapsible prosthetic heart valve is stored therein. It is therefore desirable to have systems and methods which can effectively improve the alignment of the deployed valve with the aortic annulus without significantly changing the delivery system.

In transapical valve implantation, the collapsible prosthetic heart valve is delivered in an antegrade fashion through the apex of the heart. In order to place the prosthetic heart valve accurately at the desired location in the aortic annulus, the collapsed heart valve should first expand at its annulus end. In the transapical approach, expanding the annulus end of a self-expanding prosthetic heart valve first requires the distal sheath of the delivery system to move distally toward and into the aortic arch. To allow for such movement, it is important to make the distal sheath with sufficient flexibility to accommodate the curve of the arch. On the other hand, the distal sheath should also have enough columnar strength to be able to withstand the resheathing force should resheathing become necessary. Ideally, the distal sheath design of the delivery system should strike a balance between flexibility and columnar strength. Conventional delivery systems still need to improve such balance.

SUMMARY OF THE INVENTION

The present disclosure relates to delivery systems for delivering a collapsible prosthetic heart valve. In one embodiment, the delivery system includes a valve support structure for supporting a collapsible prosthetic heart valve; and a distal sheath movable in a longitudinal direction relative to the valve support structure between a first position in which the distal sheath is adapted to surround a collapsible prosthetic heart valve supported on the valve support structure, and a second position in which the distal sheath is adapted to expose the collapsible prosthetic heart valve for deployment. The distal sheath is at least partially formed of an inner polymer layer, an outer polymer layer, and a tubular supporting member sandwiched between the inner polymer layer and the outer polymer layer.

In another embodiment, the delivery system includes a valve support structure for supporting a collapsible prosthetic heart valve; and a distal sheath preformed with a curved shape, the distal sheath being movable in a longitudinal direction relative to the valve support structure between a first position in which the distal sheath is adapted to surround a prosthetic valve supported on the valve support structure, and a second position in which the distal sheath is adapted to expose the prosthetic valve for deployment.

The present disclosure also relates to methods of manufacturing a delivery system for delivering a collapsible prosthetic heart valve. One such method includes providing a preform including a scaffold structure arranged in a tubular configuration, the preform having a curved profile; attaching at least one polymer layer to a surface of the preform to produce an assembly; placing the assembly over a curved mandrel; and applying heat to the assembly to thermally reform the at least one polymer layer in a curved shape.

Another method of manufacturing a delivery system includes placing a substantially straight distal sheath on a curved mandrel, the distal sheath including a scaffold structure arranged in a tubular configuration and at least one polymer layer attached to a surface of the scaffold structure; and heating the distal sheath to reform the distal sheath into a curved shape.

BRIEF DESCRIPTION OF THE DRAWINGS

Various embodiments of the present invention will now be described with reference to the appended drawings. It is appreciated that these drawings depict only some embodiments of the invention and are therefore not to be considered limiting of its scope.

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient.

Figure 1:
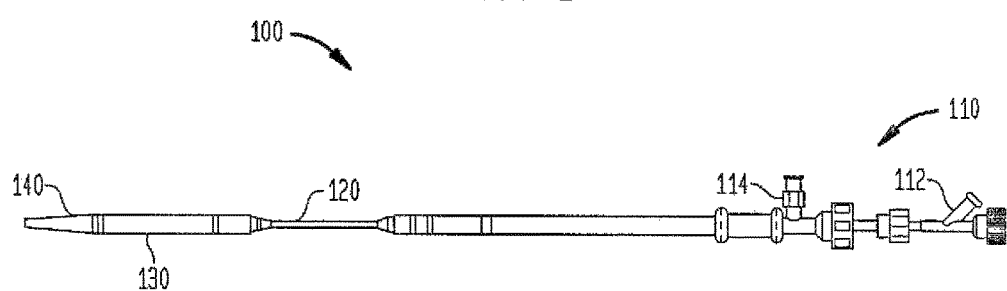
FIG. 1 is a side view of a delivery system according to an embodiment of the present disclosure, with a distal sheath in an open condition.
Figure 2:
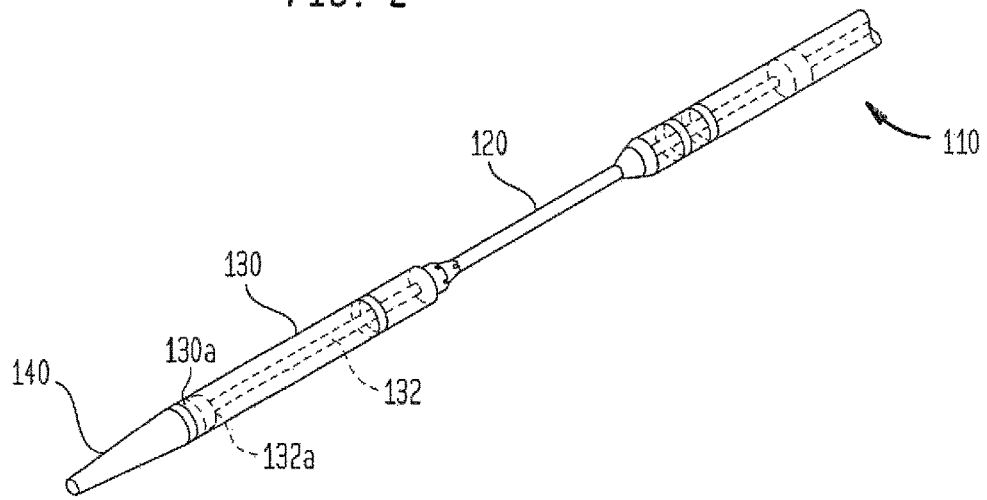
FIG. 2 is a perspective view of the distal portion of the delivery system of FIG. 1.

FIGS. 1 and 2 illustrate a delivery system 100 for transapically delivering any suitable collapsible prosthetic heart valve in a patient. Delivery system 100 generally includes a manifold 110, shaft or valve support structure 120, distal sheath 130 and distal tip 140. Shaft 120 is adapted to support a collapsible prosthetic heart valve.

As seen in FIG. 2, delivery system 100 may further include a conduit 132 extending through distal sheath 130, shaft 120 and manifold 110. The distal end 132a of conduit 132 may be connected to distal tip 140, while the proximal end (not shown) of the conduit 132 may be connected to a handle (not shown). Manifold 110 may include one or more ports 112, 114 adapted to be coupled to a source of fluid. Ports 112 and 114 may be in fluid communication with conduit 132. The distal tip 140 may have a blunt, atraumatic and/or tapered configuration and may be attached to a distal end 130a of distal sheath 130. Distal sheath 130 is movable longitudinally relative to the shaft 120 between a proximal or closed position and a distal or open position. International Patent Application Publication No. WO/2009/091509, the entire contents of which are hereby incorporated by reference, describes mechanisms for moving distal sheath 130 longitudinally with respect to the shaft 120 of delivery system 100. In the proximal position, distal sheath 130 surrounds a collapsed prosthetic heart valve mounted on shaft 120 for delivery to a target site, while in the distal position, shown in FIG. 2, the distal sheath 130 uncovers the prosthetic heart valve for deployment.

Figure 7:
FIG. 7 is a top view of the supporting member of FIG. 3.
Figure 8:
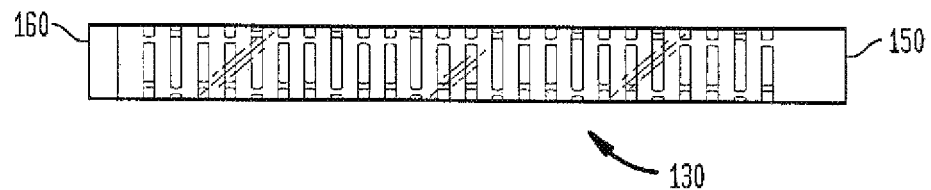
FIG. 8 is a top view of a distal sheath with the supporting member depicted in FIG. 7.

As shown in FIG. 8, distal sheath 130 may be a composite structure including a supporting member 150, an inner polymer layer (not shown) and an outer polymer layer 160, and may be dimensioned to surround at least a portion of shaft 120. The supporting member 150 of distal sheath 130 has a substantially tubular or cylindrical shape, as shown in FIG. 7. The wall thickness of supporting member 150 preferably is between about 0.002 inches and about 0.010 inches. The wall thickness of the entire distal sheath 130 is between about 0.005 inches and about 0.015 inches. The tubular wall of supporting member 150 is not solid, but rather has a pattern of cells or openings which enhance the flexibility of distal sheath 130 while maintaining its columnar strength, as will be discussed further below. Supporting member 150 may be wholly or partly formed of any suitable elastic material, such as a super-elastic shape memory material or a polymer. Examples of suitable super-elastic shape memory materials include nitinol and the like. The elastic material of the support member 150 provides the distal sheath 130 with flexibility and columnar strength.

The inner polymer layer and outer polymer layer 160 sandwich supporting member 150, enclosing the pattern of openings in the supporting member without detracting substantially from its flexibility. Outer polymer layer 160 may be wholly or partly made of any suitable polymer including, but not limited to, nylon, a polyether block amide sold by Arkema Inc. under the trademark PEBAX®, or polyurethane. The inner polymer layer may be wholly or partly made of polytetrafluoroethylene (PTFE). Regardless of the specific materials employed, the inner polymer layer may have a higher lubricity than the outer polymer layer 160 to facilitate valve deployment and resheathing, if necessary.

In addition to supporting member 150, distal sheath 130 may include braided metal wires embedded in the outer polymer layer 160 and/or the inner polymer layer to enhance the columnar strength of the sheath. The braided metal wires may be wholly or partly made of any suitable metal such as NiTi (nitinol), stainless steel, and the like.

As shown in FIGS. 3-6, the supporting member 150 may be formed with a variety of different patterns of cells. The different patterns of cells allow distal sheath 130 to be flexed in bi-directional or multi-directional ways.

Figure 3:
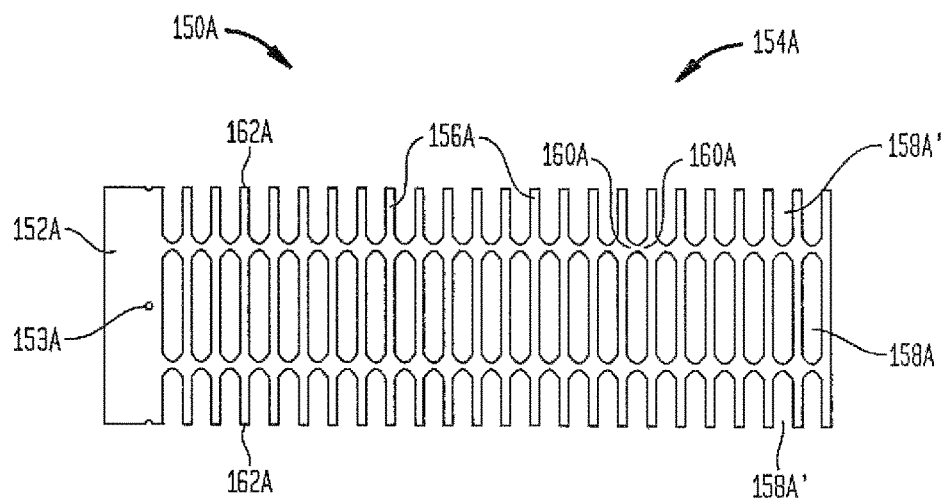
FIG. 3 is a developed view of one embodiment of a supporting member of the distal sheath shown in FIG. 1.

Referring to FIG. 3, supporting member 150A includes an array 154A of struts or columns 156A coupled to one another, with an attachment structure 152A at one end of the array. Struts 156A are oriented substantially parallel to one another and collectively form a plurality of elongated cells 158A. All of the struts 156A may have a substantially similar shape and substantially similar dimensions. Adjacent struts 156A may be joined to one another by one or more pairs of connectors 160A. Each connector 160A may have a substantially triangular shape. Two spaced connectors 160A on one strut 156A may join at their tips to the tips of two corresponding spaced connectors 160A on an adjacent strut 156A, thus providing a small surface area connection. One connector 160A may be located near the first end 162A of a strut 156A, while another connector 160A may be positioned near the second end 164A of the same strut 156A. Array 154A need not have two rows of connectors 160A, but may have a single row of connectors or more than two rows. As shown in FIG. 3, two spaced connectors 160A and the struts 156A they join may collectively form one full cell 158A and a pair of partial cells 158A', one partial cell 158N being located at the first end 162A of struts 156A, and the other partial cell 158A' being located at the second end 164A of the struts.

Attachment structure 152A may have a substantially rectangular shape and may include one or more holes 153A. Holes 153A are adapted and dimensioned to receive a pin (not shown) protruding radially from a proximal portion of distal tip 140 to facilitate attachment of distal sheath 130 to the distal tip. One or more pairs of connectors 160A may connect an adjacent strut 156A to attachment structure 152A.

In the cylindrical configuration of supporting member 150A, struts 156A extend in the circumferential direction, as do elongated cells 158A. In addition, when supporting member 150A is in the cylindrical configuration, the partial cells 158A' at the opposite ends of the struts will join to form full cells 158A. Where adjacent struts 156A are joined by two pairs of spaced connectors 160A, the connectors may all be positioned at the same distance from either the first end 162A or the second end 164A of each strut so as to form two rows of connectors which extend in the longitudinal direction of the support member 150A, substantially orthogonal to the struts 156A. One row of connectors 160A may be diametrically opposed to the other row of connectors in the cylindrical configuration of supporting member 150A. Accordingly, array 154A may provide a uniform pattern of cells 158A along the length of the support member 150A.

Where supporting member 150A includes two rows of connectors 160A, and particularly where those rows are diametrically opposed to one another in the cylindrical configuration, the pattern of cells 158A in the supporting member provides distal sheath 130 with bi-directional bending capabilities. That is, the small surface area connection between the joined connectors 160A facilitates the bending of the supporting member 150A in one direction to collapse the cells 158A on one side of the rows of connectors 160A or in the opposite direction to collapse the cells 158A on the other side of the rows of connectors. Furthermore, the alignment of connectors 160A in longitudinal rows along supporting member 150A provides distal sheath 130 with columnar strength for withstanding the resheathing force without buckling or kinking in the event resheathing is required.

Figure 4:
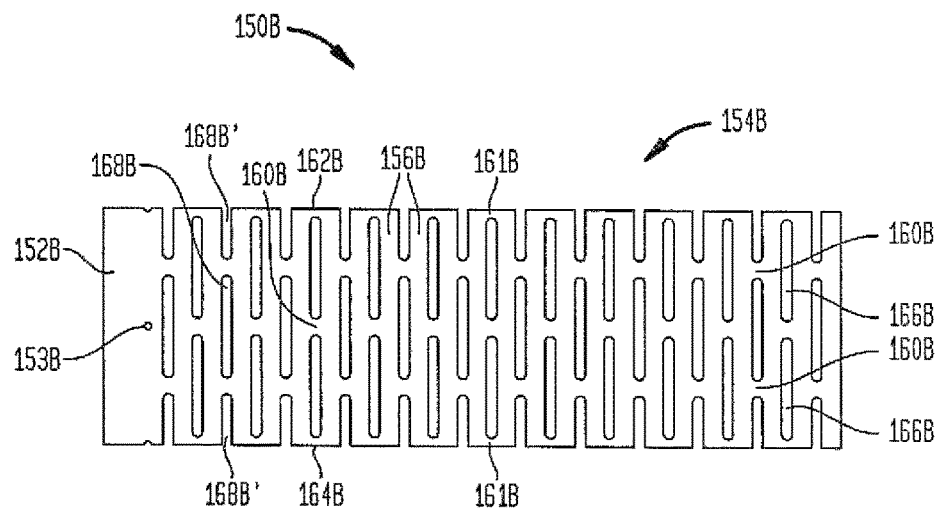
FIG. 4 is a developed view of another embodiment of the supporting member of the distal sheath depicted in FIG. 1.

With reference to FIG. 4, supporting member 150B includes an array 154B of struts 156B coupled to one another with an attachment structure 152B at one end of the array. The struts 156B of supporting member 150B are wider than the struts 156A of supporting member 150A (FIG. 3). Struts 156B are oriented substantially parallel to one another and collectively form a plurality of elongated cells 166B and 168B. All of the struts 156B may have a substantially similar shape and substantially similar dimensions.

Adjacent struts 156B may be joined to one another by one or more connectors 160B and 161B. Each connector 160B, 161B may have an hourglass shape so as to provide cells 166B and 168B with rounded ends.

Connectors 160B are positioned at alternating locations along the length of supporting member 150B. A first strut 156B may be joined to a second adjacent strut 156B by a pair of spaced connectors 160B, one connector being spaced from the first end 162B of the struts and the other connector being spaced from the second end 164B of the struts. The two spaced connectors 160B and the struts 156B they join may collectively form a full cell 168B as well as a partial cell 168B' at each end of the struts. A third strut 156B may be joined to the second strut 156B by a connector 160B positioned substantially midway between the first end 162B and the second end 164B of the struts, as well as by a pair of connectors 161B at the first and second ends of the struts. One connector 161B together with connector 160B and the struts 156B they join may collectively form one cell 166B, and the other connector 161B together with the connector 160B and the struts 156B they join may collectively form another cell 166B. The two cells 166B are arranged in end to end fashion substantially parallel to one another, with one cell 166B located closer to the first end 162B of strut 156B and the other cell 166B located closer to the second end 164B of the strut. The pattern of connectors 160B and 161B, and of cells 166B and 168B, may continue in an alternating fashion in the length direction of supporting member 150B.

Two connectors 160B may also couple attachment structure 152B to an adjacent strut 156B. These two connectors 160B together with attachment structure 152B and the adjacent strut 156B they join may form a full cell 168B and a pair of partial cells 168B'. Attachment structure 152B may include one or more holes 153B adapted and dimensioned to receive a pin (not shown) protruding radially from a proximal portion of the distal tip 140 for facilitating attachment of distal sheath 130 to the distal tip.

In the cylindrical configuration of supporting member 150B, struts 156B extend in the circumferential direction, as do elongated cells 166B and 168B. Furthermore, when supporting member 150B is in a cylindrical configuration, the connector 161B at one of a strut 156B will join with the connector 161B at the other end of the same strut 156B to form a single connector 160B, and the two partial cells 168B' at the opposite ends of a strut will join to form a full cell 168B. Where adjacent struts 156B are joined by a pair of spaced connectors 160B, these connectors may all be positioned at the same distance from either the first end 162B or the second end 164B of the struts so as to form a first two rows of connectors 160B, which alternate with cell gaps in the longitudinal direction of the supporting member 150B, substantially orthogonal to the struts 156B. Where adjacent struts 156B are joined by a connector 161B as well as a connector 160B, these connectors may all be positioned at the same distance from one another so as to form a second two rows of connectors 160B, which alternate with cell gaps in the longitudinal direction of the supporting member 150B, substantially orthogonal to the struts 156B. Therefore, in the cylindrical configuration, array 154B provides supporting member 150B with four rows of connectors extending in the longitudinal direction of the supporting member. The first two rows of connectors 160B may be diametrically opposed to one another in the cylindrical configuration of supporting member 150B, and the second two rows of connectors 160B may also be diametrically opposed to one another and offset by about 90° in the circumferential direction from the first two rows of connectors. As such, supporting member 150B in the cylindrical configuration has four rows of connectors substantially equally spaced from one another in the circumferential direction of the supporting member, with each row of connectors consisting of an alternating series of connectors and cell gaps.

The pattern of cells 166B and 168B in supporting member 150B provides distal sheath 130 with multi-directional bending capabilities. In particular, the first two rows of connectors 160B facilitate the bending of supporting member 150B in a first direction to collapse the cells 168B on one side of these rows of connectors or in a direction opposite the first direction to collapse the cells 168B on the other side of these rows of connectors. Similarly, the second two rows of connectors 160B facilitate the bending of supporting member 150B in a direction substantially orthogonal to the first direction to collapse the cells 166B on one side of these rows of connectors or in the opposite direction substantially orthogonal to the first direction to collapse the cells 166B on the other side of these rows of connectors. In total, supporting member 150B allows the distal sheath 130 to bend in at least four directions. However, since less than about one-half as many cells are available to collapse in each direction as compared to supporting member 150A, supporting member 150B provides somewhat less flexibility. Moreover, as struts 156B are wider than struts 156A in the longitudinal direction of the supporting member, there is more solid material in the longitudinal direction and necessarily less open cell area. This also has the effect of reducing flexibility.

The longitudinal rows of connectors 160B provide distal sheath 130 with substantial columnar strength. However, since the connectors 160B in each row are interposed with cell gaps, the column strength of supporting member 150B may be less than that of supporting member 150A. Despite this, the alignment of connectors 160B in four longitudinal rows distributes any axial forces exerted on supporting member 150B more uniformly than in supporting member 150A.

Figure 5:
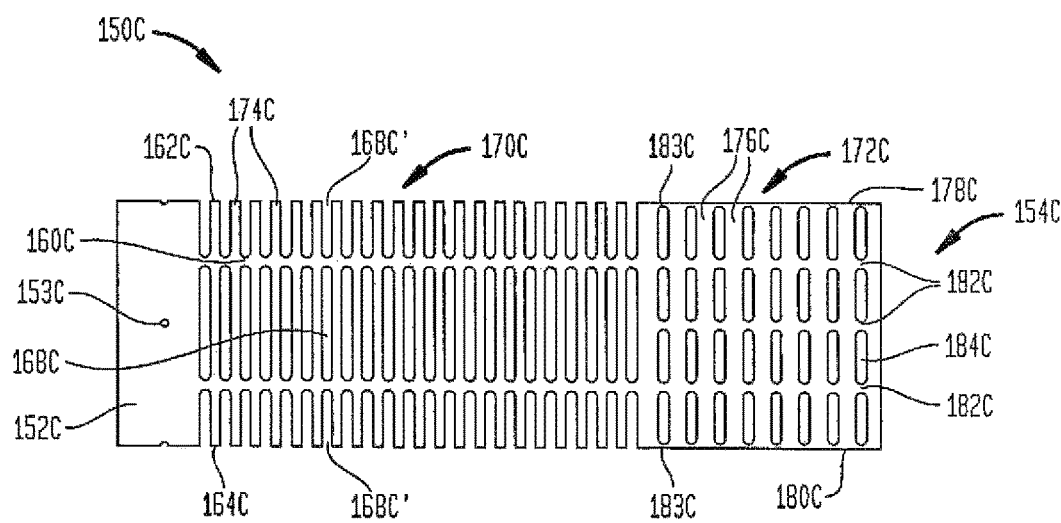
FIG. 5 is a developed view of yet another embodiment of the supporting member of the distal sheath illustrated in FIG. 1.

Referring to FIG. 5, supporting member 150C includes an array 154C of struts 174C and 176C with an attachment structure 152C at one end of the array. Array 154C has a first or distal section 170C and a second or proximal section 172C with different kinds of struts. The struts 174C of the first section 170C are thinner in the longitudinal direction of the supporting member than the struts 176C of the second section 172C. Consequently, the first section 170C of the array 154C has more open cell area than the second section 172C. This difference tends to provide the first section 170C of the array 154C with more flexibility than the second section 172C.

The struts 174C are oriented substantially parallel to one another and collectively form a plurality of elongated full cells 168C in the first section 170C, as well as a plurality of partial cells 168C' on either side of the full cells. All of the struts 174C may have a substantially similar shape and substantially similar dimensions. Adjacent struts 174C may be joined to one another by one or more spaced connectors 160C. Each connector 160C may have a substantially hourglass shape so as to provide cells 168C with rounded ends. One connector 160C may be located near the first end 162C of a strut 174C, while another connector 160C may be positioned near the second end 164C of the same strut 174C. The first section 170C of array 154C need not have two rows of connectors 160C, but may have a single row of connectors or more than two rows. In addition to joining adjacent struts 174C to one another, connectors 160C may also join the first section 170C of struts to the second section 172C of struts.

The struts 176C in the second section 172C are oriented substantially parallel to one another and to struts 174C. Struts 176C may all have a substantially similar shape and substantially similar dimensions, and collectively form a plurality of elongated cells 184C. Adjacent struts 176C may be joined to one another by three connectors 182C and two connectors 183C. Each connector 182C may have a substantially hourglass shape so as to form cells 184C with rounded edges. One connector 183C may be positioned at the first end 178C of a strut 176C, while another connector 183C may be positioned at the second end 180C of the strut. The other three connectors 182C may be positioned between the first end 178C and the second end 180C of each strut 176C. These three connectors 182C may be spaced the same distance from one another and from the first and second ends of each strut 176C.

Attachment structure 152C may have a substantially rectangular shape and may include one or more holes 153C adapted and dimensioned to receive a pin (not shown) protruding radially from a proximal portion of the distal tip 140 for attaching the distal sheath 130 to the distal tip. One or more spaced connectors 160C may connect an adjacent strut 174C to attachment structure 152C. The connectors 160C together with the attachment structure 152C and the strut 174C they join may form a full cell 168C and a pair of partial cells 168C' on either side thereof.

In the cylindrical configuration of supporting member 150C, struts 174C of the first section 170C of array 154C extend in the circumferential direction, as do elongated cells 168C. In addition, the pair of partial cells 168C' on the ends 162C and 164C of struts 174C will join to form a full cell 168C. Where adjacent struts 174C are joined to a pair of spaced connectors 160C, the connectors may all be positioned at the same distance from either the first end 162C or the second end 164C of each strut so as to form two rows of connectors which extend in the longitudinal direction of the supporting member 150C, substantially orthogonal to the struts 174C. One row of connectors 160C may be diametrically opposed to the other row of connectors in the cylindrical configuration of supporting member 150C. Accordingly, the first section 170C of array 154C may have a uniform pattern of cells 168C extending in the length direction of supporting member 150C.

In the cylindrical configuration of supporting member 150C, struts 176C of the second section 172C of array 154C also extend in the circumferential direction, as do elongated cells 184C. Furthermore, when supporting member 150C is in a cylindrical configuration, the connector 183C at one end of a strut 176C will join with the connector 183C at the other end of the same strut to form a single connector 182C. Connectors 182C may all be positioned at the same distance from either the first end 178C or the second end 180C of the struts so as to form four rows of connectors which extend in the longitudinal direction of the supporting member 150C, substantially orthogonal to the struts 176C. Accordingly, in the cylindrical configuration, the second section 172C of array 154C provides four rows of connectors extending in the longitudinal direction of the supporting member. The connectors 182C in each row may be diametrically opposed to the connectors in another row, and the rows of connectors may be spaced apart by about 90° in the circumferential direction. Furthermore, the connectors 182C in one pair of rows may be aligned in the longitudinal direction with the rows of connectors 160C in section 170C of supporting member 150C.

The pattern of connectors 160C and cells 168C in supporting member 150C provides distal sheath 130 with columnar strength and bi-directional bending capabilities at least along the length covered by the first section 170C of the array 154C, similar to that obtained with supporting member 150A described above. Additionally, the pattern of connectors 182C and cells 184C in supporting member 150C provides distal sheath 130 with multi-directional bending capabilities at least along the length covered by the second section 172C of array 154C. In particular, two opposed rows of connectors 182C facilitate the bending of the second section 172C in a first direction to collapse cells 184C on one side of these rows of connectors or in a direction opposite the first direction to collapse the cells 184C on the other side of these rows of connectors. Similarly, the other two opposed rows of connectors 182C facilitate the bending of the second section 172C in a second direction substantially orthogonal to the first direction to collapse the cells 184C on one side of these rows of connectors or in a direction opposite the second direction to collapse the cells 184C on the other side of these rows of connectors. In total, the pattern of cells 184C in the second section 172C of array 154C allows distal sheath 130 to bend in four different directions. It will be appreciated, however, that these four directions are offset by about 45° in the circumferential direction from the directions in which the first section 170C of supporting member 150C may bend because of the locations of connectors 182C. Moreover, the greater number of connectors 182C in each circumferential row causes the second section 172C to have somewhat less flexibility than the first section 170C. Also, as struts 176C are wider than struts 174C in the longitudinal direction of the supporting member, there is more solid material in the longitudinal direction in the second section 172C than in the first section 170C and necessarily less open cell area. This also has the effect of reducing the flexibility of the second section relative to the first section.

The different widths of the struts 174C and 176C as well as the different patterns of connectors 160C and 182C also provides distal sheath 130 with varying columnar strength. However, as the rows of connectors 160C align longitudinally with two of the rows of connectors 182C without the interposition of any cell gaps, supporting member 150C has superior columnar strength to supporting member 150B described above. Moreover, the alignment of connectors 182C in four longitudinal rows in the second section 172C of supporting member 150C causes the second section to distribute any axial forces exerted on the supporting member more uniformly than the first section 170C, enabling the proximal portion of distal sheath 130 to distribute the axial forces more evenly than the distal portion thereof.

Figure 6:
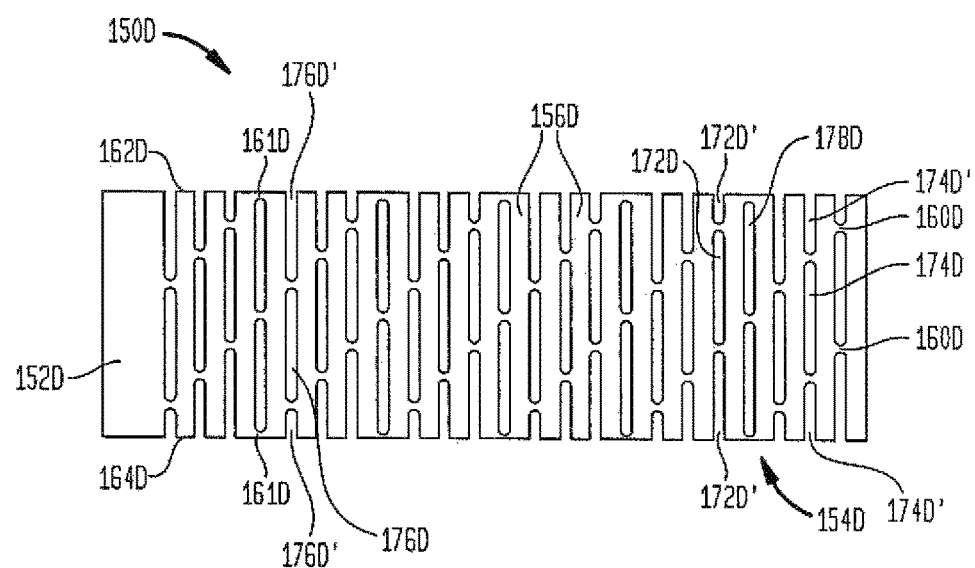
FIG. 6 is a developed view of a further embodiment of the supporting member of the distal sheath shown in FIG. 1.

With reference to FIG. 6, supporting member 150D includes an array 154D of struts 156D coupled to one another with an attachment structure 152D at one end of the array. Struts 156D are oriented substantially parallel to one another and collectively form a plurality of elongated cells 172D, 174D, 176D and 178D. All of the struts 156D may have a substantially similar shape and substantially similar dimensions. Adjacent struts 156D may be joined to one another by one or more pairs of connectors 160D and 161D. Each connector 160D, 161D may have a substantially hourglass shape so as to form cells 172D, 174D, 176D and 178D with rounded ends.

Connectors 160D are positioned at staggered locations along the length of supporting member 150D. That is, a first strut 156D may be joined to a second adjacent strut 156D by a pair of spaced connectors 160D, one connector being spaced from the first end 162D of the struts and the other connector being spaced by a greater distance from the second end 164D of the struts. The two spaced connectors 160D and the struts 156D they join may collectively form a full cell 172D as well as a partial cell 172D' at each end of the struts. A third strut 156D may be joined to the second strut 156D by a second pair of spaced connectors 160D, the connectors being equally spaced from the first end 162D and the second end 164D of the struts. The two spaced connectors 160D and the struts 156D they join may collectively form a full cell 174D as well as a partial cell 174D' at each end of the struts. A fourth strut 156D may be joined to the third strut 156D by a pair of spaced connectors 160D, one connector being spaced from the first end 162D of the struts and the other connector being spaced by a lesser distance from the second end 164D of the struts. The two spaced connectors 160D and the struts 156D they join may collectively form a full cell 176D as well as a partial cell 176D' at each end of the struts. A fifth strut 156D may be joined to the fourth strut 156D by a connector 160D positioned substantially midway between the first end 162D and the second end 164D of the struts, as well as pair by a pair of connectors 161D at the first and second ends of the struts. One connector 161D together with connector 160D and the struts 156D they join may collectively form one full cell 178D, and the other connector 161D together with the connector 160D and the struts 156D they join may collectively form another full cell 178D. The two cells 178D are arranged in end to end fashion substantially parallel to one another, with one cell 178D located closer to the first end 162D of strut 156D and the other cell 178D located closer to the second end 164D of the strut. The pattern of connectors 160D, 161D, and of cells 172D, 172D', 174D, 174D', 176D, 176D', and 178D, may continue in an alternating fashion in the length direction of supporting member 150D.

Attachment structure 152D may have a substantially rectangular shape and may include one or more holes (not shown) adapted and dimensioned to receive a pin (not shown) protruding radially from the distal tip 140 to facilitate attachment of the supporting member 150D to the distal tip 140. Two connectors 160D may connect attachment structure 152D to an adjacent strut 156D. These two connectors 160D together with the adjacent strut 156D and the attachment structure 152D they join may form a full cell 176D and a pair of partial cells 176D', or any of the other cells 172D, 174D or 178D described above.

In the cylindrical configuration of supporting member 150D, struts 156D extend in the circumferential direction, as do elongated cells 172D, 174D, 176D and 178D. Additionally, when supporting member 150D is in the cylindrical configuration, the connector 161D at one end of a strut 156D will join with the connector 161D at the other end of the same strut to form a single connector 160D, and the partial cells 172D', 174D' and 176D' at the ends of the struts will join to form full cells 172D, 174D and 176D, respectively. The spaced connectors 160D forming cells 172D may all be positioned at the same distance from either the first end 162D or the second end 164D of the struts so as to form the first two rows of connectors 160D substantially orthogonal to the struts, in which the connectors are spaced from one another in the longitudinal direction of the supporting member 150D by three cell gaps. Similarly, the spaced connectors 160D forming cells 174D may all be positioned at the same distance from either the first or second end of the struts so as to form a second two rows of connectors 160D substantially orthogonal to the struts, in which the connectors 160D are separated in the longitudinal direction by three cell gaps. Also, the spaced connectors 160D forming cells 176D may all be positioned at the same distance from the first and second ends of the struts so as to form a third two rows of connectors 160D substantially orthogonal to the struts, again with the connectors being spaced from one another in the longitudinal direction by three cell gaps. Finally, where adjacent struts 156D are joined by connectors 161D as well as a connector 160D, these connectors may all be positioned at the same distance from one another so as to form a fourth two rows of connectors 160D substantially orthogonal to the struts, with the connectors spaced from one another in the longitudinal direction of the supporting member by three cell gaps. Therefore, in the cylindrical configuration, array 154D provides supporting member 150D with eight rows of connectors extending in the longitudinal direction of the supporting member. In the cylindrical configuration, the first two rows of connectors 160D may be diametrically opposed to one another; the second two rows of connectors 160D may also be diametrically opposed to one another and offset by about 45° in the circumferential direction from the first two rows of connectors; the third two rows of connectors 160D may also be diametrically opposed to one another and offset by about 90° in the circumferential direction from the first two rows of connectors; and the fourth two rows of connectors 160D may be diametrically opposed to one another and offset by about 135° in the circumferential direction from the first two rows of connectors. As such, supporting member 150D has eight rows of connectors substantially equally spaced from one another in the circumferential direction of the supporting member, with each row of connectors consisting of individual connectors alternating with three adjacent cell gaps.

The pattern of cells 172D, 174D, 176D and 178D in supporting member 150D provides distal sheath 130 with multi-directional bending capabilities. In particular, the first two rows of connectors 160D facilitate the bending of the supporting member 150D in a first direction to collapse the cells 172D on one side of these rows of connectors or in a direction opposite the first direction to collapse the cells 172D on the other side of these rows of connectors. Similarly, the third two rows of connectors 160D facilitate the bending of supporting member 150D in a second direction substantially orthogonal to the first direction to collapse the cells 176D on one side of these rows of connectors or in a direction opposite the second direction to collapse the cells 176D on the other side of these rows of connectors. In addition, the second two rows of connectors 160D facilitate the bending of supporting member 150D in a third direction intermediate the first and second directions to collapse the cells 174D on one side of these rows of connectors or in a direction opposite the third direction to collapse the cells 174D on the other side of these rows of connectors, and the fourth two rows of connectors 160D facilitate the bending of the supporting member in a fourth direction intermediate the second and first directions to collapse the cells 176D on one side of these rows of connectors or in a direction opposite the fourth direction to collapse the cells 176D on the other side of these rows of connectors. In total, supporting member 150D allows the distal sheath 130 to bend in at least eight directions. However, since much fewer cells are available to collapse in each direction as compared to supporting member 150B described above, supporting member 150D provides less flexibility. Moreover, the larger number of cell gaps between connectors 160D in the longitudinal direction has the effect of lowering the overall columnar strength of supporting member 150D as compared to the columnar strength of supporting member 150B, although the axial forces exerted on the supporting member are distributed more uniformly than in the supporting member embodiments described above.

Delivery system 100 can be used for implanting a collapsible prosthetic heart valve using the transapical approach. A prosthetic heart valve is first mounted on the shaft 120 of the delivery system in a collapsed condition, and distal sheath 130 is moved proximally over the heart valve to maintain it in the collapsed condition and protect it during delivery into a patient.

In the transapical approach, the delivery system 100 is inserted through the apex of the patient's heart and advanced until the distal sheath 130 is positioned in the native aortic valve. Once so positioned, the distal sheath 130 may be moved distally relative to shaft 120 to uncover the prosthetic heart valve for deployment. Because of the patterns of cells in the supporting member (150A, 150B, 150C or 150D), the distal sheath 130 is able to flex as it is advanced into and through the aortic arch. As distal sheath 130 moves distally, the exposed proximal end of the prosthetic heart valve will expand until it engages the aortic valve annulus. The physician can then determine whether the prosthetic heart valve is properly positioned. If so, the distal movement of the distal sheath 130 can resume until the prosthetic heart valve has been fully deployed and is free from the delivery system 100, at which point the distal sheath can be moved proximally to its original position and the delivery system removed from the patient. If, on the other hand, the physician determines that the prosthetic heart valve is not properly positioned in the aortic annulus prior to its full deployment, the distal sheath 130 may be moved proximally to again collapse and cover the proximal end of the heart valve, enabling the delivery system 100 to be repositioned and deployment to again be initiated.

Figure 9:
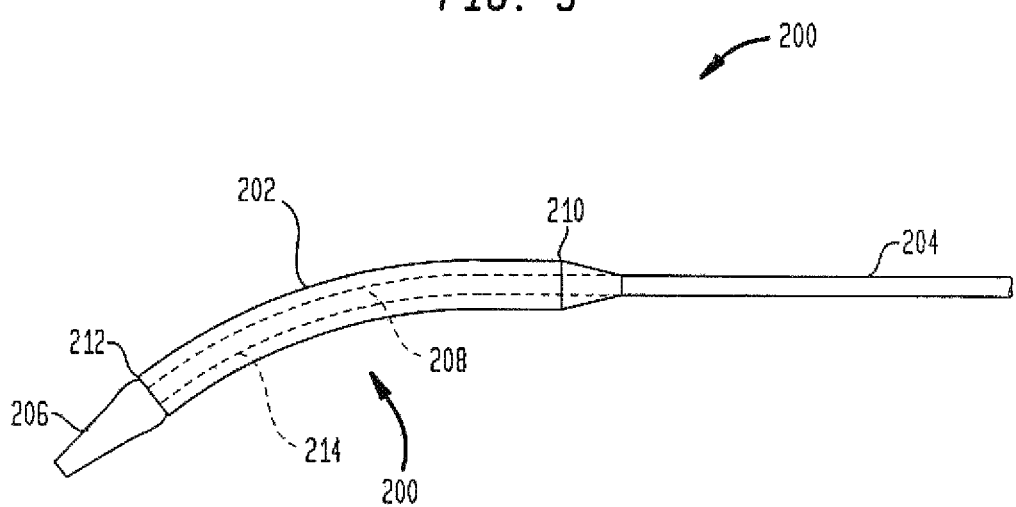
FIG. 9 is a top view of the distal portion of a delivery system having a curved distal sheath.

FIG. 9 shows a distal section 200 of a delivery system, particularly for transfemorally delivering any suitable collapsible prosthetic heart valve into a patient. The distal section 200 of the delivery system includes an elongated conduit 204, a distal sheath 202 attached to conduit 204, a valve support structure or shaft 208 surrounded by distal sheath 202, and a distal tip 206. Distal sheath 202 has an overall curved shape. However, a portion of the distal sheath 202, such as adjacent proximal end 210, may have a straight or linear configuration. The delivery system may include a marker, such as a radiopaque stripe (not shown), disposed longitudinally on the catheter shaft or handle to indicate the direction of the pre-set curve. The distal end 212 of distal sheath 202 is configured to abut, but is not attached to, the distal tip 206. Distal tip 206 may have an atraumatic and/or tapered configuration.

Distal sheath 202 is movable relative to shaft 208 between a distal or closed position, as shown in FIG. 9, and a proximal or open position. International Patent Application Publication No. WO/2009/091509, the entire disclosure of which is hereby incorporated herein by reference, describes mechanisms for moving distal sheath 202 with respect to the shaft 208 of the delivery system. In the distal position, as shown in FIG. 9, distal sheath 202 surrounds a collapsed prosthetic heart valve mounted on shaft 208 for delivery to a target site, whereas in the proximal position, the distal sheath 202 uncovers the prosthetic heart valve for deployment.

Figure 10:
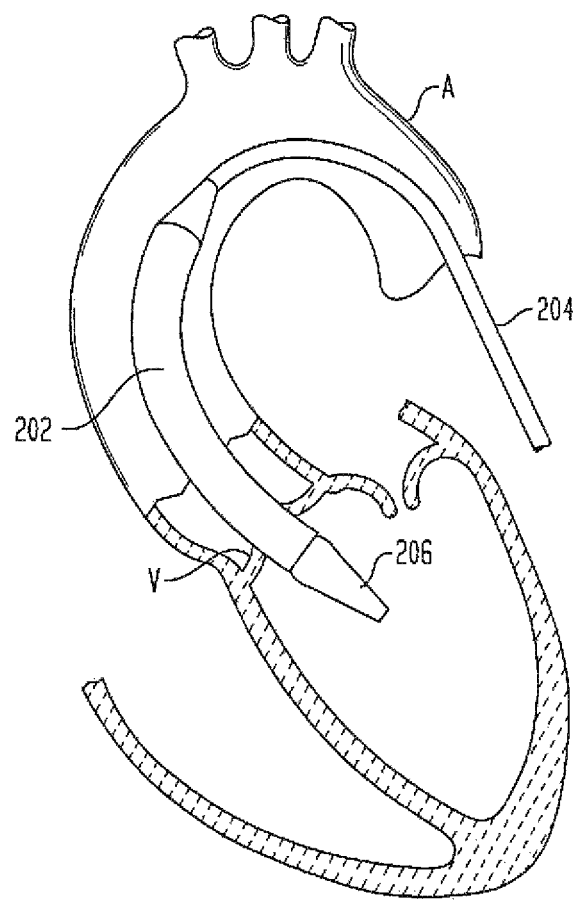
FIG. 10 is a highly schematic view of the curved distal sheath shown in FIG. 9 positioned at a patient's native aortic valve.

The radius of curvature of distal sheath 202 may be between about 2 inches and about 3 inches, for example, 2.5 inches. A radius of curvature less than 2 inches may hinder resheathing. On the other hand, a radius of curvature greater than 3 inches may not improve the ability of the distal sheath 202 to deploy the collapsible prosthetic heart valve in proper alignment with the native aortic annulus. The curved profile of distal sheath 202 facilitates delivery of the prosthetic heart valve by allowing the distal sheath to easily travel along the aortic arch of the patient, as shown in FIG. 10. Accordingly, the prosthetic heart valve can be easily aligned with the native aortic valve annulus when deployed with a delivery system having curved distal sheath 202.

Figure 11:
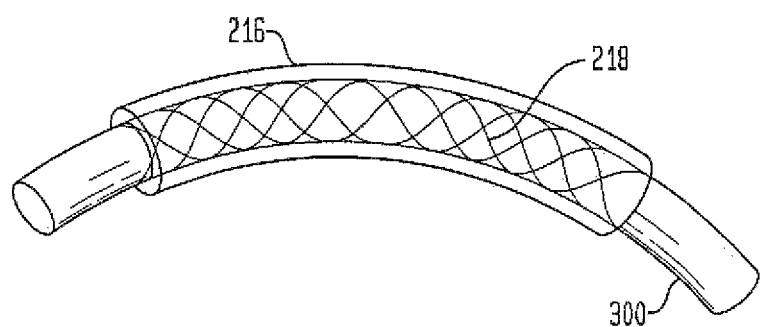
FIG. 11 is a highly schematic perspective view of a polymeric layer and braided wires placed on a mandrel, illustrating an exemplary method of making the distal sheath.

Referring to FIG. 11, distal sheath 202 may include an outer polymer layer 216, a layer of braided metal wires 218, and an inner polymer layer (not shown). The layer of braided metal wires 218 may be sandwiched between the outer polymer layer 216 and the inner polymer layer. In lieu of the layer of braided metal wires 218, the distal sheath 202 may include any of the supporting members (e.g., 150A, 150B, 150C, or 150D) described above sandwiched between the outer polymer layer 216 and the inner polymer layer. The outer polymer layer 216 may be wholly or partly formed of nylon, a polyether block amide sold by Arkema France under the trademark PEBAX®, polyurethane, or the like. The Shore durometer hardness of the outer polymer layer 216 may be from about 35D to about 72D. The inner polymer layer may be wholly or partly made of polytetrafluoroethylene (PTFE).

The valve support structure or shaft 208 of the delivery system can support a prosthetic heart valve and has a curved section 214. The length of the curved section 214 may be between about 0.5 inches and about 4 inches. The radius of curvature of curved section 214 may be between about 2 inches and about 3 inches. Preferably, the radius of curvature of curved section 214 of the shaft 208 is substantially the same as the radius of curvature of the distal sheath 202. As with curved distal sheath 202, the curved portion 214 of shaft 208 facilitates delivery of the prosthetic heart valve by allowing the shaft to easily travel along the aortic arch of the patient, as well as within the distal sheath. Shaft 208 may be formed of any suitable polymer, such as polybutylene terephthalate (PBT).

Several manufacturing methods may be employed to form distal sheath 202. With reference to FIG. 11, one exemplary method involves heating a braided distal sheath 202 on a curved mandrel 300. In this exemplary method, the braided metal wires 218 are pre-set in a curved shape. The curved braided metal wires 218 are then positioned between an outer polymer layer 216 and an inner polymer layer. The resulting combination is placed on the curved mandrel 300 and subjected to any suitable thermal forming process, such as thermal reflow. Irrespective of the specific thermal forming process employed, the outer polymer layer 216 and the inner polymer layer are heated until they acquire the curved shape of the mandrel 300 and then allowed to cool.

Figure 12:
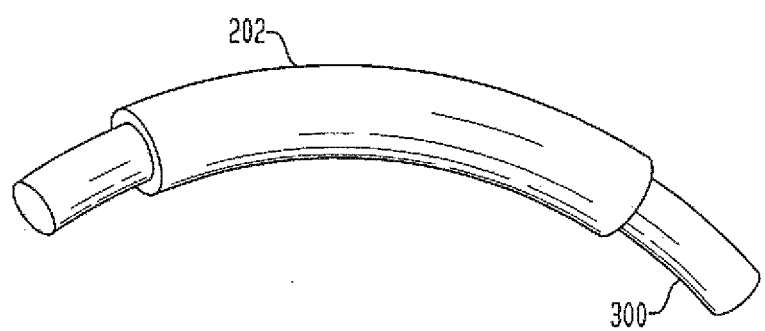
FIG. 12 is a highly schematic perspective view of a distal sheath on a mandrel, illustrating an alternate method of making the distal sheath.

With reference to FIG. 12, in an alternate manufacturing method, a straight distal sheath 202 is made using any conventional process. The straight distal sheath 202 is then positioned over curved mandrel 300. Curved mandrel 300 and distal sheath 202 are subsequently subjected to a heating process suitable to form distal sheath 202 in a curved configuration. For example, distal sheath 202 and curved mandrel 300 may be heated at about 200-300° F. in an oven for a period of time sufficient for annealing of the braided metal wires. The distal sheath 202 is then allowed to cool. By employing this manufacturing method, the stresses in the braided metal wires and polymer layers will be significantly reduced. This method simplifies the manufacturing process of the delivery system, but produces a distal sheath 202 which may be less stable than that produced using the method described above.

As illustrated in FIG. 10, a delivery system with a curved distal sheath 202 can be used for implanting a collapsible prosthetic heart valve using the transfemoral approach. A prosthetic heart valve is first mounted on the shaft 208 of the delivery system in a collapsed condition, and distal sheath 202 is moved distally over the heart valve to keep it in the collapsed condition and protect it during delivery into a patient.

In the transfemoral approach, the delivery system is inserted through the aorta A of the patient in a retrograde manner until the distal sheath 202 is positioned in the native aortic valve V. At this point, the distal sheath 202 of the delivery system may be moved proximally relative to the shaft 208 to uncover the prosthetic heart valve for deployment. As the distal sheath 202 moves proximally, the exposed distal end of the prosthetic heart valve expands until it engages the aortic valve annulus. The physician can then determine whether the prosthetic heart valve is properly positioned. If so, the proximal movement of the distal sheath 202 can resume until the prosthetic heart valve has been fully deployed and is free from the delivery system, at which point the distal sheath 202 can be moved distally to its initial position and the delivery system removed from the patient. However, if the physician determines that the prosthetic heart valve is not properly positioned in the aortic annulus prior to its full deployment, the distal sheath 202 may be moved distally to again collapse and cover the distal end of the heart valve, enabling the delivery system to be repositioned and deployment to again be initiated.

Since the curved distal sheath 202 can travel along the aortic arch without much difficulty, it is easier to achieve proper planar alignment of the prosthetic heart valve with the native aortic annulus. Also, because of its curved shape, distal sheath 202 may be formed of a stiffer material with higher columnar strength to better withstand the high resheathing forces.

Although the present disclosure mainly describes the use of the delivery system depicted in FIG. 9 for transfemorally delivering a collapsible prosthetic heart valve, this delivery system also may be employed in a transapical procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A delivery device for implanting a prosthetic heart valve, comprising:
   a valve support for supporting a collapsible prosthetic heart valve; and
   a distal sheath slidable in a longitudinal direction relative to the valve support between a first position in which the distal sheath is adapted to maintain the prosthetic heart valve in a collapsed condition, and a second position in which the distal sheath is adapted to expose the prosthetic heart valve for deployment, the distal sheath including an inner polymer layer, an outer polymer layer, and a tubular support sandwiched between the inner polymer layer and the outer polymer layer, the tubular support having a first longitudinal section and a second longitudinal section and including a plurality of struts extending in a circumferential direction of the tubular support, each of the first and second longitudinal sections having a degree of flexibility sufficient to facilitate advancement of the distal sheath into the aortic arch, the degree of flexibility of the first longitudinal section being different than the degree of flexibility of the second longitudinal section, each strut defining a continuous closed loop, the loops being coupled to one another by a plurality of connectors so as to define a plurality of open cells, the connectors in the first longitudinal section being arranged in a plurality of linear rows oriented substantially orthogonally to the loops, the connectors in the second longitudinal section being arranged in a plurality of linear rows oriented substantially orthogonally to the loops, the connectors in the first longitudinal section being joined to the loops in the first longitudinal section so as to define continuous structures extending from one end of the first longitudinal section to another end of the first longitudinal section, the connectors in the second longitudinal section being joined to the loops in the second longitudinal section so as to define continuous structures extending from one end of the second longitudinal section to another end of the second longitudinal section, each of the continuous structures in the first longitudinal section being continuous and colinear with a respective one of the continuous structures in the second longitudinal section, each of the continuous structures in the second longitudinal section being diametrically opposed to another of the continuous structures in the second longitudinal section.

2. The delivery device as claimed in claim 1, wherein each of the loops in the second longitudinal section has a selected width in the longitudinal direction and each of the loops in the first longitudinal section has a width in the longitudinal direction that is less than the selected width.

3. The delivery device as claimed in claim 1, wherein each of the continuous structures in the first longitudinal section is diametrically opposed to another of the continuous structures in the first longitudinal section.

4. The delivery device as claimed in claim 1, wherein the second longitudinal section has a greater number of rows of connectors than the first longitudinal section.

5. The delivery device as claimed in claim 4, wherein the first longitudinal section includes exactly two rows of connectors.

6. The delivery device as claimed in claim 5, wherein the second longitudinal section includes exactly four rows of connectors.

7. The delivery device as claimed in claim 1, wherein the degree of flexibility of the first longitudinal section is greater than the degree of flexibility of the second longitudinal section.

8. The delivery device as claimed in claim 1, wherein the plurality of open cells defines an open cell area in the second longitudinal section and an open cell area in the first longitudinal section that is greater than the open cell area in the second longitudinal section.

9. The delivery device as claimed in claim 1, wherein the first longitudinal section is connected to the second longitudinal section by a plurality of section connectors.

10. The delivery device as claimed in claim 9, wherein each of the section connectors is aligned in the longitudinal direction with a respective one of the continuous structures in the second longitudinal section.

11. The delivery device as claimed in claim 10, wherein each of the section connectors is aligned in the longitudinal direction with a respective one of the continuous structures in the first longitudinal section.

12. The delivery device as claimed in claim 11, wherein each of the continuous structures in the first longitudinal section is continuous with a respective one of the section connectors.

13. The delivery device as claimed in claim 1, wherein the inner polymer layer has a higher lubricity than the outer polymer layer.

14. The delivery device as claimed in claim 1, wherein the continuous structures in the second longitudinal section are equally spaced apart from one another in the circumferential direction of the tubular support.

* * * * *